United States Patent [19]

Hiratsuka et al.

[11] Patent Number: 5,101,076
[45] Date of Patent: Mar. 31, 1992

[54] β-HYDROXYKETONE AND ITS PRODUCTION

[75] Inventors: Mitsunori Hiratsuka, Takarazuka; Masao Shiroshita, Osaka; Susumu Ohtsuka, Takarazuka; Kenji Arai, Toyonaka; Naonori Hirata, Sakai, all of Japan

[73] Assignee: Sumitomo Chemical Company, Limited, Osaka, Japan

[21] Appl. No.: 700,267

[22] Filed: May 15, 1991

Related U.S. Application Data

[62] Division of Ser. No. 292,258, Dec. 30, 1988, Pat. No. 5,041,679.

[30] Foreign Application Priority Data

Jan. 7, 1988 [JP] Japan ............................. 63-001647
Feb. 12, 1988 [JP] Japan ............................. 63-031369
Mar. 1, 1988 [JP] Japan ............................. 63-049050

[51] Int. Cl.$^5$ ............................................ C07C 323/09
[52] U.S. Cl. ............................................ 568/43; 568/42
[58] Field of Search ............................ 568/43, 42

[56] References Cited

FOREIGN PATENT DOCUMENTS 1157948 6/1989 Japan ............................... 568/43

OTHER PUBLICATIONS

Chemical Abstracts, vol. 100, No. 5, 30 Jan. 1984, p. 389, Abstract No. 33776u.
Chemical Abstracts, vol. 94, 1981, Abstract No. 94:120871x Nippon Soda.

*Primary Examiner*—Marianne Cintins
*Assistant Examiner*—Margaret Argo
*Attorney, Agent, or Firm*—Stevens, Davis, Miller & Mosher

[57] ABSTRACT

Compounds of the present invention are represented by the formula,

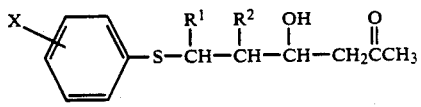

wherein X represents a lower alkyl, lower alkoxy, lower haloalkyl or lower haloalkoxy group or a halogen atom, and $R^1$ and $R^2$, which may be the same or different, represent a hydrogen atom or a methyl group. They are useful intermediates for preparing herbicidal compounds.

2 Claims, No Drawings

β-HYDROXYKETONE AND ITS PRODUCTION

This is a division of application Ser. No. 07/292,258, filed Dec. 30, 1988 now U.S. Pat. No. 5,041,679.

The present invention relates to a novel β-hydroxyketone [hereinafter referred to as hydroxyketone(s) (I)] and its production and use.

The hydroxyketones of the present invention are represented by the formula (I),

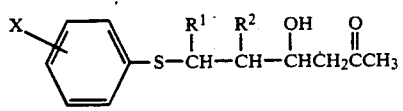

wherein X represents a lower alkyl, lower alkoxy, lower haloalkyl or lower haloalkoxy group or a halogen atom, and $R^1$ and $R^2$, which may be the same or different, represent a hydrogen atom or a methyl group. The term "lower" means a group having 1 to 4 carbon atoms.

The hydroxyketones of the present invention (I) are useful intermediates for the production of 5-substituted-1-hydroxy-3-oxocyclohex-1-ene derivatives represented by the formula (II),

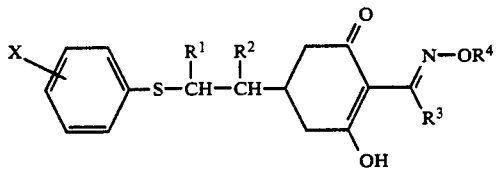

wherein X, $R^1$ and $R^2$ have the same meanings as defined above, $R^3$ represents a lower alkyl group, and $R^4$ represents a lower alkyl, lower alkenyl, lower alkynyl or lower haloalkenyl group, said derivatives themselves being effective as herbicides (See EP-253537A, EP-254514A and U.S. Pat. No. 4,249,937).

The herbicidal compounds represented by the foregoing formula (II) can be produced through the route described below, where Wittig reaction is necessary to be carried out. However, particularly in practicing the reaction on industrial scales, the process has encountered such problems that the Wittig reagent is expensive, the efficiency of liquid-liquid separation at the after-treatment of the reaction is low and a phosphorus-containing waste water should be purified before draining.

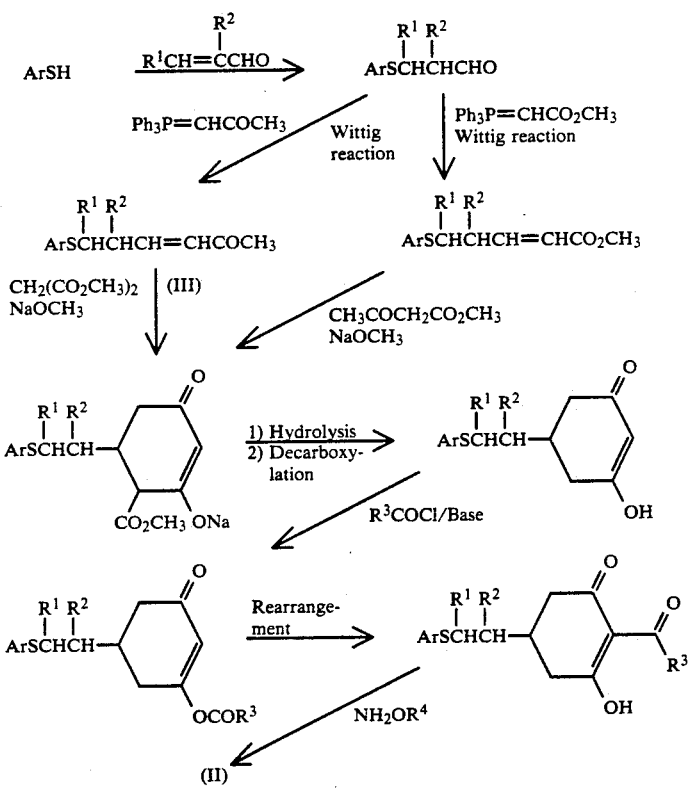

wherein Ar represents

and $R^1$, $R^2$, $R^3$, $R^4$ and X have the same meanings as defined above.

The present inventors have studied an advantageous method for producing the herbicidal compounds represented by the formula (II), particularly α,β-unsaturated ketone compounds represented by the formula (III),

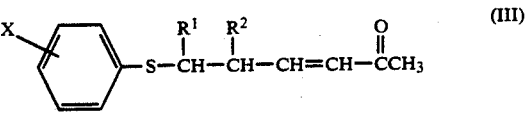

wherein X, R¹ and R² have the same meanings as defined above. As a result, they have found that the foregoing hydroxyketones (I) are useful intermediates, and that the α,β-unsaturated ketone compounds (III) can be produced advantageously by dehydrating the hydroxyketones (I) in the presence of at least one acid selected from the group consisting of oxalic acid, acetic acid, trichloroacetic acid, sulfuric acid, p-toluenesulfonic acid, boric acid, metaboric acid, phosphoric acid, polyphosphoric acid, silica gel and acidic polymers (e.g. Nafion ®; a registered trade mark of E. I. du Pont de Nemours and Co.).

They have also found that the hydroxyketones (I) can be produced advantageously by allowing to react an aldehyde compound represented by the formula (IV),

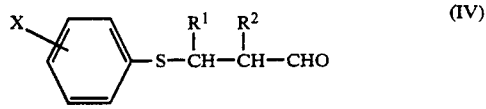

wherein X, R¹ and R² have the same meanings as defined above, with an acetoacetic acid salt in the presence of a $C_1$–$C_6$ carboxylic acid salt and optionally a phase transfer catalyst.

GB-A-2075972 discloses a process for producing some of the α,β-unsaturated ketone compounds (III). Said process, however, is disadvantageous because it produces many by-products.

Specific examples of X contained in the foregoing formulae are 2-methyl, 3-methyl, 4-methyl, 2-ethyl, 3-ethyl, 4-ethyl, 2-propyl, 3-propyl, 4-propyl, 2-isopropyl, 3-isopropyl, 4-isopropyl, 2-butyl, 3-butyl, 4-butyl, 2-methoxy, 3-methoxy, 4-methoxy, 2-ethoxy, 3-ethoxy, 4-ethoxy, 2-propoxy, 3-propoxy, 4-propoxy, 2-isopropoxy, 3-isopropoxy, 4-isopropoxy, 2-butoxy, 3-butoxy, 4-butoxy, 2-fluoro, 3-fluoro, 4-fluoro, 2-chloro, 3-chloro, 4-chloro, 2-bromo, 3-bromo, 4-bromo, 2-iodo, 3-iodo, 4-iodo, 2-difluoromethyl, 3-difluoromethyl, 4-difluoromethyl, 2-trifluoromethyl, 3-trifluoromethyl, 4-trifluoromethyl, 2-trifluoromethoxy, 3-trifluoromethoxy, 4-trifluoromethoxy, 2-(1,1,2,2-tetrafluoroethoxy), 3-(1,1,2,2-tetrafluoroethoxy), 4-(1,1,2,2-tetrafluoroethoxy), etc.

A process for producing the hydroxyketones (I) will be described below.

The hydroxyketones (I) are produced by allowing to react an aldehyde compound (IV) with an acetoacetic acid salt in the presence of a $C_1$–$C_6$ carboxylic acid salt and optionally a phase transfer catalyst.

The reaction temperature is generally from 0° to 100° C., usually from 10° to 60° C., and the reaction time is usually from 30 minutes to 24 hours.

The reaction is usually carried out in a two-layer mixture of water and an organic solvent in the presence of a phase transfer catalyst. The organic solvent used includes for example halogenated hydrocarbons (e.g. dichloromethane, chloroform, dichloroethane), aromatic hydrocarbons (e.g. benzene, toluene, xylene), etc. Still, a phase transfer catalyst is not always necessary. For example, it is not necessary when a mixture of water and a lower alcohol (e.g. methanol, ethanol) is used as a solvent.

In the reaction, hydrogencarbonate anions are formed in the reaction mixture as shown in the following reaction formula:

$$Y-CHO + CH_3COCH_2CO_2^- \longrightarrow Y-\overset{\underset{\displaystyle |}{OH}}{C}HCH_2COCH_3 +$$

$HCO_3^-$ wherein Y represents 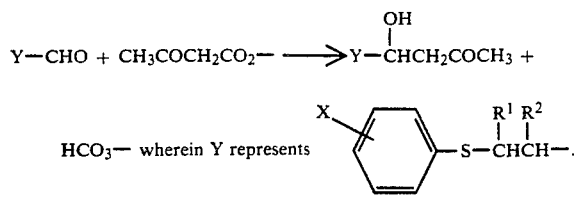

The reaction proceeds smoothly when the reaction mixture is adjusted to pH 6 to 8 by adding a suitable acid (e.g. hydrochloric acid) thereto, if necessary, which acid decomposes the hydrogencarbonate anions. After the reaction has been completed, the organic layer is separated (in this case, an acid such as hydrochloric acid is added if necessary) from the reaction mixture and treated as usual to obtain the hydroxyketone compound. The compound may be purified by recrystallization, chromatography, etc.

The acetoacetic acid salts used in the process are alkali metal salts (e.g. sodium salt, potassium salt) of acetoacetic acid, for example. These salts may be formed in the reaction system in situ by hydrolyzing the acetoacetic acid esters.

Specific examples of the $C_1$–$C_6$ carboxylic acid salts are the alkali metal salts (e.g. sodium salt, potassium salt) or ammonium salts of formic acid, acetic acid, propionic acid, n-butyric acid, isobutyric acid, n-valeric acid, isovaleric acid, etc. Specific examples of the phase transfer catalysts are ammonium salts such as tetrabutylammonium bromide, benzyltriethylammonium chloride; sulfonic acid salts such as sodium dodecylbenzenesulfonate; phosphonium salts such as cetyltributylphosphonium bromide; and amines such as tris-[2-(2-methoxyethoxy)ethyl]amine. The carboxylic acid salt may be used in an amount sufficient to catalytically encourage the reaction, usually not less than 0.05 mole, and generally 0.1–0.2 mlle per mole of the aldehyde compound represented by the formula (III). The phase transfer catalyst may be optionally used. When it is used, it may be used in an amount sufficient to catalytically encourage the reaction, usually not less than 0.05 mole, and generally 0.1–0.2 mole per mole of the aldehyde compound.

Explanation will be given to the dehydration for producing the α,β-unsaturated ketone compounds (III) from the hydroxyketones (I).

The dehydration is carried out in the presence of at least one acid selected from the group consisting of oxalic acid, acetic acid, trichloroacetic acid, sulfuric acid, p-toluenesulfonic acid, boric acid, metaboric acid, phosphoric acid, polyphosphoric acid, silica gel and acidic polymers (e.g. Nafion ®; a registered trade mark of E. I. du Pont de Nemours and Co.). Usually, the reaction is carried out in a solvent and at a temperature of from room temperature to the boiling point of the solvent used. The reaction time is from about 30 minutes to about 10 hours. The solvent used includes for example halogenated hydrocarbons (e.g. chloroform, dichloroethane, chlorobenzene), hydrocarbons (e.g. benzene, toluene, xylene), etc. The acid is used in an amount sufficient to catalytically encourage the reaction. It is usually used in an amount not less than 0.01 mole, generally about 0.2 mole per mole of the hydroxyketones (I) used.

After the reaction has been completed, the reaction solution is washed, concentrated, etc. as usual. If necessary, the product may be chromatographed, recrystallized, etc.

The present invention will be illustrated with reference to the following production examples and comparative examples, but it is not limited to these production examples only.

First, production examples for the hydroxyketones (I) will be shown.

PRODUCTION EXAMPLE 1

9.86 Grams of methyl acetoacetate were dissolved in 15 ml of water, and 12.67 g of a 30% aqueous sodium hydroxide solution was added thereto by drops while cooling the mixture to 20° C. or less. After having been stirred at 30°-35° C. for 3 hours, the mixture was adjusted to pH 7.0 by adding a concentrated aqueous hydrochloric acid solution thereto. Thereafter, 1.47 g of sodium acetate and then a concentrated aqueous hydrochloric acid solution was added to the mixture so that the mixture had a pH of 6.8. And 50 ml of methanol and then 8.72 g of 3-(4-chlorophenylthio)propanal were added thereto. After having been stirred at 45°-50° C. for 8 hours, the mixture was filtered. The filtrate was concentrated under reduced pressure, and the residue obtained was extracted with ethyl acetate. The organic layer was washed with a 5% aqueous acetic acid solution and then with a saturated aqueous sodium chloride solution. Then the layer was dried over anhydrous magnesium sulfate. Removing the solvent from the layer under reduced pressure gave 13.26 g of crude 6-(4-chlorophenylthio)-4-hydroxy-2-hexanone (purity: 92.3%, yield 91.4%). A purified product was obtained by recrystallization from diisopropyl ether-hexane. The purified product had a melting point of 46.0°-47° C.

PRODUCTION EXAMPLE 2

19.72 Grams of methyl acetoacetate were dissolved in 30 ml of water, and 25.33 g of a 30% aqueous sodium hydroxide solution were added thereto by drops while cooling the mixture to 25° C. or less. After having been stirred at 30°-35° C. for 3 hours, the mixture was adjusted to pH 7.0 with a concentrated aqueous hydrochloric acid solution. Thereafter, 0.98 g of sodium acetate and then an additional concentrated aqueous hydrochloric acid solution were added to the mixture so that the mixture had a pH of 6.9. And 40 ml of methanol and then 23.44 g of 3-(4-trifluoromethylphenylthio)propanal were added thereto. The resulting mixture was stirred at 45°-50° C. for 10 hours. The mixture was concentrated under reduced pressure, and the residue obtained was extracted three times with ethyl acetate. The organic layers were combined, washed twice with a 5% aqueous acetic acid solution and then twice with a saturated aqueous sodium chloride solution and thereafter dried over anhydrous magnesium sulfate. Removing the solvent from the washed layer under reduced pressure gave 22.64 g of crude 4-hydroxy-6-(4-trifluoromethylphenylthio)-2-hexanone (purity: 89.6%, yield: 69.4%).

PRODUCTION EXAMPLE 3

9.86 Grams of methyl acetoacetate were dissolved in 15 ml of water, and 12.67 g of a 30% aqueous sodium hydroxide solution was added thereto by drops while cooling the mixture to 25° C. or less. After having been stirred at 30°-35° C. for 3 hours, the mixture was adjusted to pH 7.0 with a concentrated aqueous hydrochloric acid solution. Thereafter, 1.07 g of sodium isovalerate and 2.42 g of tetrabutylammonium bromide were added thereto. Then a concentrated aqueous hydrochloric acid solution was added to the mixture so that the mixture had a pH of 6.8. Further, 26.2 g of a toluene solution containing 32.7% of 3-(2-methylphenylthio)propanal was added thereto and stirred at 45°-50° C. for 9 hours. The organic layer separated from the mixture was washed with a 5% aqueous acetic acid solution and then with a saturated aqueous sodium chloride solution. Thereafter the layer was dried over anhydrous magnesium sulfate. Removing the solvent from the layer under reduced pressure gave 10.32 g of crude 4-hydroxy-6-(2-methylphenylthio)-2-hexanone (purity: 67.8%, yield: 62.1%). A purified product was obtained by column chromatography. The purified product had an $n_D^{21}$ of 1.5660.

PRODUCTION EXAMPLE 4

9.86 Grams of methyl acetoacetate was dissolved in 15 ml of water, and 12.67 g of a 30% aqueous sodium hydroxide solution was added thereto by drops while cooling the mixture to 25° C. or less. After having been stirred at 30°-35° C. for 3 hours, the mixture was adjusted to pH 7.0 with a concentrated aqueous hydrochloric acid solution. Thereafter, 0.68 g of sodium formate and 2.42 g of tetrabutylammonium bromide were added thereto. Thereafter a concentrated aqueous hydrochloric acid solution was added to the resulting mixture so that the mixture had a pH of 6.8. Further, 27.2 g of a toluene solution containing 35.1% of 3-(2-methylphenylthio)butanal was added thereto and stirred at 45°-50° C. for 9 hours. The organic layer separated from the mixture was washed with a 5% aqueous acetic acid solution and then with a saturated aqueous sodium chloride solution. Thereafter the layer was dried over anhydrous magnesium sulfate. Removing the solvent from the layer under reduced pressure gave 12.44 g of crude 4-hydroxy-6-(2-methylphenylthio)-2-heptanone (purity: 85.1%, yield: 85.3%). A purified product was obtained by column chromatography. The purified product had an $n_D^{21}$ of 1.5477.

PRODUCTION EXAMPLE 5

4.93 Grams of methyl acetoacetate were dissolved in 7.5 ml of water, and 6.34 g of a 30% aqueous sodium hydroxide solution were added thereto by drops while cooling the mixture to 25° C. or less. After having been stirred at 30°-35° C. for 3 hours, the mixture was adjusted to pH 7.0 with a concentrated aqueous hydrochloric acid solution. Thereafter, 0.30 g of sodium acetate and 1.00 g of tetrabutylammonium bromide were added thereto and then an additional hydrochloric acid was added thereto so that the mixture had a pH of 6.9. Further, 17.8 g of a toluene solution containing 27.5% of 3-(2-methoxyphenylthio)propanal were added thereto and the resulting mixture was stirred at 45°-50° C. for 9 hours. The organic layer was separated from the mixture. It was washed with a 5% aqueous acetic acid solution and then with a saturated aqueous sodium chloride solution. Then it was dried over anhydrous magnesium sulfate. Removing the solvent from the layer under reduced pressure gave 5.78 g of crude 4-hydroxy-6-(2-methoxyphenylthio)-2-hexanone (purity: 79.9%, yield: 75.7%). A purified product was obtained by column chromatography. The purified product had an $n_D^{21}$ of 1.5705.

PRODUCTION EXAMPLE 6

9.86 Grams of methyl acetoacetate were dissolved in 15 ml of water, and 12.67 g of a 30% aqueous sodium hydroxide solution was added thereto by drops while cooling the mixture to 25° C. or less. After having been stirred at 30°-35° C. for 3 hours, the mixture was adjusted to pH 7.0 with a concentrated aqueous hydrochloric acid solution. Thereafter, 0.74 g of potassium acetate and 2.42 g of tetrabutylammonium bromide were added thereto, and then an additional concentrated aqueous hydrochloric acid was added thereto so that the mixture had a pH of 6.9. Further, 28.00 g of a toluene solution containing 38.0% of 3-(3-methoxyphenylthio)butanal were added thereto and the resulting mixture was stirred at 45°-50° C. for 9 hours. The organic layer separated from the mixture was washed with a 5% aqueous acetic acid solution and then with a saturated aqueous sodium chloride solution. Then it was dried over anhydrous magnesium sulfate. Removing the solvent from the layer under reduced pressure gave 13.39 g of crude 4-hydroxy-6-(3-methoxyphenylthio)-2-heptanone (purity 90.9%, yield: 89.6%). A purified product was obtained by column chromatography. The purified product had an $n_D^{21}$ of 1.5530.

PRODUCTION EXAMPLE 7

9.86 Grams of methyl acetoacetate were dissolved in 15 ml of water, and 12.67 g of a 30% aqueous sodium hydroxide solution were added thereto by drops while cooling the mixture to 25° C. or less. After having been stirred at 30°-35° C. for 3 hours, the mixture was adjusted to pH 7.0 with a concentrated aqueous hydrochloric acid solution. Thereafter, 0.76 g of ammonium acetate and 2.42 g of tetrabutylammonium bromide were added, and then an additional concentrated aqueous hydrochloric acid solution was added thereto so that the mixture was controlled to have a pH of 6.8. Further, 28.00 g of a toluene solution containing 33.6% of 3-(4-methoxyphenylthio)butanal were added thereto and the resulting mixture was stirred at 45°-50° C. for 9 hours. The organic layer separated from the mixture was washed with a 5% aqueous acetic acid solution and then with a saturated aqueous sodium chloride solution. Then it was dried over anhydrous magnesium sulfate. Removing the solvent from the layer under reduced pressure gave 12.04 g of crude 4-hydroxy-6-(4-methoxyphenylthio)-2-heptanone (purity: 53.3%, yield: 53.6%). A purified product was obtained by column chromatography. The purified product had an $n_D^{21}$ of 1.5428.

PRODUCTION EXAMPLE 8

10 9 86 Grams of methyl acetoacetate were dissolved in 15 ml of water, and 12.67 g of a 30% aqueous sodium hydroxide solution were added thereto by drops while cooling the mixture to 25° C. or less. After having been stirred at 30°-35° C. for 3 hours, the mixture was adjusted to pH 7.0 with a concentrated aqueous hydrochloric acid solution. Thereafter, 0.62 g of sodium acetate and 2.42 g of tetrabutylammonium bromide were added thereto and then an additional concentrated aqueous hydrochloric acid solution was added thereto so that the mixture had a pH of 6.9. Further, 27.4 g of a toluene solution containing 36.6% of 3-(3-fluorophenylthio)butanal were added thereto and the resulting mixture was stirred at 45°-50° C. for 9 hours. The organic layer separated from the mixture was washed with a 5% aqueous acetic acid solution and then with a saturated aqueous sodium chloride solution. Then it was dried over anhydrous magnesium sulfate. Removing the solvent from the layer under reduced pressure gave 12.49 g of crude-6-(3-fluorophenylthio)-4-hydroxy-2-heptanone (purity: 90.8%, yield: 87.4%). A purified product was obtained by column chromatography. The purified product had an $n_D^{21}$ of 1.5342.

PRODUCTION EXAMPLE 9

5 9.86 Grams of methyl acetoacetate were dissolved in 15 ml of water, and 12.67 g of a 30% aqueous sodium hydroxide solution was added dropwise while cooling the mixture to not higher than 25° C. After having been stirred at 30°-35° C. for 3 hours, the mixture was adjusted to pH 7.0 with a concentrated aqueous hydrochloric acid solution. Thereafter, 0.49 g of sodium acetate and 2.42 g of tetrabutylammonium bromide were added thereto and then an additional conc. hydrochloric acid was added thereto to control the mixture to pH 6.8-6.9. Further, 27.1 g of a toluene solution containing 36.5% of 3-(4-fluorophenylthio)-2-methylpropanal were added thereto and the resulting mixture was stirred at 45°-50° C. for 8 hours. The organic layer was separated, washed with a 5% aqueous acetic acid solution and then with a saturated aqueous sodium chloride solution and then dried over anhydrous magnesium sulfate. The solvent was removed under reduced pressure to obtain a crude 6-(4-fluorophenylthio)-4-hydroxy-5-methyl-2-hexanone. A purified product was obtained by column chromatography in a yield of 40 2%. The purified product had an $n_D^{21}$ of 1.5396.

PRODUCTION EXAMPLE 10

9.86 Grams of methyl acetoacetate were dissolved in 15 ml of water, and 12.67 g of a 30% aqueous sodium hydroxide solution were added thereto by drops while cooling the mixture to 25° C. or less. After having been stirred at 30°-35° C. for 3 hours, the mixture was adjusted to pH 7.0 with a concentrated aqueous hydrochloric acid solution. Thereafter, 0.49 g of sodium acetate and 2.42 g of tetrabutylammonium bromide were added thereto and then an additional concentrated aqueous hydrochloric acid solution was added to the mixture so that the mixture was adjusted to pH 6.8 to 6.9. Further, 27.93 g of a toluene solution containing 38.4% of 3-(3-chlorophenylthio)-2-methylpropanal were added thereto and was stirred at 45°-50° C. for 8 hours. The organic layer separated from the mixture was washed with a 5% aqueous acetic acid solution and then with a saturated aqueous sodium chloride solution. Then the layer was dried over anhydrous magnesium sulfate. Removing the solvent from the layer under reduced pressure gave a crude 6-(3-chlorophenylthio)-4-hydroxy-5-methyl-2-hexanone. A purified product was obtained by column chromatography in a yield of 46.5%. The purified product had an $n_D^{21}$ of 1.5647.

PRODUCTION EXAMPLE 11

15.10 Grams of methyl acetoacetate were dissolved in 20 ml of water, and 18.20 g of a 30% aqueous sodium hydroxide solution were added thereto by drops while cooling the mixture to 25° C. or less. After having been stirred at 30°-35° C. for 3 hours, the mixture was adjusted to pH 7.0 with a concentrated aqueous hydrochloric acid solution. Thereafter, 0.82 g of sodium acetate and 3.22 g of tetrabutylammonium bromide were added thereto and then an additional concentrated aqueous hydrochloric acid solution was added to the mixture so that the mixture was adjusted to pH 6.9. Further, 54.45 g of a toluene solution containing 36.8% of 3-(4-chlorophenylthio)propanal were added thereto and was stirred at 45°-50° C. for 6 hours. The organic layer separated from the layer was washed with a 5% aqueous acetic acid solution and then with a saturated aqueous sodium chloride solution. Then the layer was dried over anhydrous magnesium sulfate. Removing the solvent from the layer under reduced pressure gave 27.08 g of crude 6-(4-chloro-phenylthio)-4-hydroxy-2-hexanone (purity: 87.83%, yield: 92.0%).

PRODUCTION EXAMPLE 12

9.86 Grams of methyl acetoacetate were dissolved in 15 ml of water, and 12.67 g of a 30% aqueous sodium hydroxide solution were added thereto by drops while cooling the mixture to 25° C. or less. After having been stirred at 30°-35° C. for 3 hours, the mixture was adjusted to pH 7.0 with a concentrated aqueous hydrochloric acid solution. Thereafter, 1.10 g of sodium butyrate and 2.42 g of tetrabutylammonium bromide were added thereto and then an additional concentrated aqueous hydrochloric acid solution was added to the mixture so that the mixture was adjusted to pH 6.8. Further, 29.45 g of a toluene solution containing 31.2% of 3-(4-bromophenylthio)propanal were added thereto and was stirred at 45°-50° C. for 9 hours. The organic layer separated from the mixture was washed with a 5% aqueous acetic acid solution and then with a saturated aqueous sodium chloride solution. Then the layer was dried over anhydrous magnesium sulfate. Removing the solvent from the layer under reduced pressure gave 14.54 g of crude 6-(4-bromophenylthio)-4-hydroxy-2-hexanone (purity: 81.8%, yield: 99.5%). A purified product was obtained by recrystallization from diisopropyl ether. The purified product had a melting point of 53.0°-54.0° C.

PRODUCTION EXAMPLE 13

3.77 Grams of methyl acetoacetate were dissolved in 5 ml of water, and 4.50 g of a 30% aqueous sodium hydroxide solution was added thereto by drops while cooling the mixture to 35° C. or less. After having been stirred at 30°-35° C. for 3 hours, the mixture was adjusted to pH 7.5 with 50% sulfuric acid. Thereafter, 0.31 g of sodium acetate and 0.81 g of tetrabutylammonium bromide were added thereto and 14.7 g of a toluene solution containing 39.8% of 3-(4-trifluoromethylphenylthio)propanal were added thereto. The mixture was stirred at 45°-50° C. for 6 hours and then at room temperature for 12 hours. After the mixture had been neutralized with a 50% sulfuric acid, the organic layer was separated, washed with a saturated aqueous sodium chloride solution and then dried over anhydrous magnesium sulfate. Removing the solvent from the layer under reduced pressure gave 6.82 g of crude 4-hydroxy-6-(4-trifluoromethylphenylthio)2-hexanone (purity, 92.6%). The crude product was further recrystallized from diisopropyl ether to obtain 6.04 g of a purified product. The yield of the purified product was 82.7%. It had a melting point of 73.0°-74.5° C.

PRODUCTION EXAMPLE 14

1.51 Grams of methyl acetoacetate were dissolved in 2 ml of water, and 1.82 g of a 30% aqueous sodium hydroxide solution were added thereto by drops while cooling the mixture to 35° C. or less. After having been stirred at 30°-35° C. for 6 hours, the mixture was adjusted to pH 7.5 with a concentrated aqueous hydrochloric acid solution. Thereafter, 0.08 g of sodium acetate and 0.32 g of tetrabutylammonium bromide were added thereto and then 5.82 g of a toluene solution containing 40.2% of 3-(4-trifluoromethylphenylthio)propanal were added thereto. The mixture was stirred at 30°-35° C. for 6 hours and then at room temperature for 12 hours. After the mixture had been neutralized with a concentrated aqueous hydrochloric acid solution, the organic layer was separated, washed with a saturated aqueous sodium chloride solution and then dried over anhydrous magnesium sulfate. Removing the solvent from the layer under reduced pressure gave 3.10 g of crude 4-hydroxy-6-(4-trifluoromethylphenylthio)-2-hexanone (purity: 73.1%, yield 77.6%).

PRODUCTION EXAMPLE 15

1.51 Grams of acetoacetic acid were dissolved in 2 ml of water, and 1.82 g of a 30% aqueous sodium hydroxide solution were added thereto by drops while cooling the mixture to 35° C. or less. After having been stirred at 30°-35° C. for 6 hours, the mixture was adjusted to pH 7.5 with a concentrated aqueous hydrochloric acid solution. Thereafter, 0.08 g of sodium acetate and 0.32 g of tetrabutylammonium bromide were added thereto and then 5.82 g of a toluene solution containing 40.2% of 3-(4-trifluoromethylphenylthio)propanal were added thereto. The mixture was stirred at 45°-50° C. for 6 hours and then at room temperature for 12 hours. After the mixture had been neutralized with a concentrated aqueous hydrochloric acid solution, the organic layer was separated, washed with a saturated aqueous sodium chloride solution and then dried over anhydrous magnesium sulfate. Removing the solvent from the layer under reduced pressure gave 3.02 g of crude 4-hydroxy-6-(4-trifluoromethylphenylthio)-2-hexanone (purity: 82.8%, yield: 85.6%).

PRODUCTION EXAMPLE 16

The same procedure as in Production example 14 was repeated except that the amount of sodium acetate was changed from 0.08 g to 0.16 g, and that the amount of tetrabutylammonium bromide was changed from 0.32 g to 0.64 g. Thus, 3.24 g of crude 4-hydroxy-6-(4-trifluoromethylphenylthio)-2-hexanone was obtained (purity: 85.0%, yield: 94.3%).

PRODUCTION EXAMPLE 17

15.1 Grams of methyl acetoacetate were dissolved in 20 ml of water, and 18.2 g of a 30% aqueous sodium hydroxide solution were added thereto by drops while cooling the mixture to 35° C. or less. After having been stirred at 30°-35° C. for 3 hours, the mixture was adjusted to pH 7.5 with a concentrated aqueous hydrochloric acid solution. Thereafter, 0.82 g of sodium acetate and 3.22 g of tetrabutylammonium bromide were added thereto and then 54.85 g of a toluene solution containing 36.6% of 3-(4-trifluoromethylphenylthio)propanal were added thereto. The mixture was stirred at 45°-50° C. for 6 hours. After the mixture had been neutralized with a concentrated aqueous hydrochloric acid solution, the organic layer was separated, washed with a saturated aqueous sodium chloride solution and then dried over anhydrous magnesium sulfate. Removing the solvent from the layer under reduced pressure gave 27.08 g of crude 4-hydroxy-6-(4-trifluoromethylphenylthio)-2-hexanone (purity: 87.8%, yield: 92.0%).

PRODUCTION EXAMPLE 18

7.55 Grams of methyl acetoacetate were dissolved in 10 ml of water, and 9.1 g of a 30% aqueous sodium hydroxide solution were added thereto by drops while cooling the mixture to 35° C. or less. After having been stirred at 30°–35° C. for 3 hours, the mixture was adjusted to pH 7.5 with a concentrated aqueous hydrochloric acid solution. Thereafter, 0.35 g of sodium formate and 1.61 g of tetrabutylammonium bromide were added thereto and then 54.0 g of a toluene solution containing 17.4% of 3-(4-trifluoromethylphenylthio)-propanal were added thereto. The mixture was stirred at 45°–50° C. for 10 hours and then at room temperature for 4 hours. After the mixture had been neutralized with a concentrated aqueous hydrochloric acid solution, the organic layer was separated, washed with a saturated aqueous sodium chloride solution and then dried over anhydrous magnesium sulfate. Removing the solvent from the layer under reduced pressure gave 14.88 g of crude 4-hydroxy-6-(4-trifluoromethylphenylthio)2-hexanone (purity: 74.5%, yield: 75.9%).

PRODUCTION EXAMPLE 19

7.55 Grams of methyl acetoacetate were dissolved in 10 ml of water, and 9.1 g of a 30% aqueous sodium hydroxide solution were added thereto by drops while cooling the mixture to 35° C. or less. After having been stirred at 30°–35° C. for 3 hours, the mixture was adjusted to pH 7.5 with a concentrated aqueous hydrochloric acid solution. Thereafter, 0.32 g of ammonium formate and 1.61 g of tetrabutylammonium bromide were added thereto and then 54.0 g of a toluene solution containing 17.4% of 3-(4-trifluoromethylphenylthio)-propanal were added thereto. The mixture was stirred at from 45°–50° C. for 10 hours and then at room temperature for 12 hours. After the mixture had been neutralized with a concentrated aqueous hydrochloric acid solution, the organic layer was separated, washed with a saturated aqueous sodium chloride solution and then dried over anhydrous magnesium sulfate. Removing the solvent from the layer under reduced pressure gave 13.90 g of crude 4-hydroxy-6-(4-trifluoromethylphenylthio)-2-hexanone (purity: 81.4%, yield: 77.5%).

PRODUCTION EXAMPLE 20

The same procedure as in Production example 18 was repeated except that 0.50 g of potassium acetate was used in place of 0.35 g of sodium formate. Thus, 14.60 g of crude 4-hydroxy-6-(4-trifluoromethylphenylthio)-2-hexanone were obtained (purity: 74.0%, yield: 74.0%).

PRODUCTION EXAMPLE 21

The same procedure as in Production example 19 was repeated except that 0.39 g of ammonium acetate was used in place of 0.32 g of ammonium formate. Thus, 14.02 g of crude 4-hydroxy-6-(4-trifluromethylphenylthio)-2-hexanone were obtained (purity: 79.5%, yield: 76.2%).

PRODUCTION EXAMPLE 22

The same procedure as in Production example 18 was repeated except that 0.55 g of sodium n-butyrate was used in place of 0.35 g of sodium formate. Thus, 15.25 g of crude 4-hydroxy-6-(4-trifluoromethylphenylthio)-2-hexanone were obtained (purity 76.3%, yield 79.7%).

PRODUCTION EXAMPLE 23

The same procedure as in Production example 18 was repeated except that 0.71 g of sodium isovalerate was used in place of 0.35 g of sodium formate. Thus, 14.55 g of crude 4-hydroxy-6-(4-trifluoromethylphenylthio)2-hexanone were obtained (purity: 84.9%, yield: 84.6%).

PRODUCTION EXAMPLE 24

7.54 Grams of methyl acetoacetate were dissolved in 10 ml of water, and 9.07 g of a 30% aqueous sodium hydroxide solution were added thereto by drops while cooling the mixture to 35° C. or less. After having been stirred at 30°–35° C. for 3 hours, the mixture was adjusted to pH 7.5 with a concentrated aqueous hydrochloric acid solution. Thereafter, 0.41 g of sodium acetate and 1.61 g of tetrabutylammonium bromide were added thereto and then 29.4 g of a toluene solution containing 33.8% of 3-(3-trifluoromethylphenylthio)-propanal were added thereto. The mixture was stirred at 45°–50° C. for 6 hours. After the mixture had been neutralized with a concentrated aqueous hydrochloric acid solution, the organic layer was separated, washed with a saturated aqueous sodium chloride solution and then dried over anhydrous magnesium sulfate. Removing the solvent from the layer under reduced pressure gave 14.92 g of crude 4-hydroxy-6-(3-trifluoromethylphenylthio)-2-hexanone (purity: 80.2%, yield: 96.7%).

A purified product was obtained by column chromatography and recrystallization from diisopropyl ether. The purified product had a melting point of 40 0°–43.0°.

PRODUCTION EXAMPLE 25

15.1 Grams of methyl acetoacetate were dissolved in 20 ml of water, and 19.4 g of a 28% aqueous sodium hydroxide solution were added thereto by drops while cooling the mixture to 35° C. or less. After having been stirred at 30°–35° C. for 2 hours, the mixture was adjusted to pH 7.5 with a concentrated aqueous hydrochloric acid solution. Thereafter, 0.82 g of sodium acetate and 3.22 g of tetrabutylammonium bromide were added thereto and then 60.3 g of a toluene solution containing 36.9% of 3-(2-trifluoromethylphenylthio)-propanal were added thereto. The mixture was stirred at 45°–50° C. for 6 hours. After the mixture had been neutralized with a concentrated aqueous hydrochloric acid solution, the organic layer was separated, washed with a saturated aqueous sodium chloride solution and then dried over anhydrous magnesium sulfate. Removing the solvent from the layer under reduced pressure gave 31.10 g of crude 4-hydroxy-6-(2-trifluoromethylphenylthio)-2-hexanone (purity: 83.7%, yield: 93.7%).

A purified product was obtained by column chromatography. The purified product had an $n_D^{22}$ of 1.5191.

PRODUCTION EXAMPLE 26

10.56 Grams of methyl acetoacetate were dissolved in 14 ml of water, and 13.9 g of a 28% aqueous sodium hydroxide solution were added thereto by drops while cooling the mixture to 35° C. or less. After having been stirred at 30°–35° C. for 3 hours, the mixture was adjusted to pH 7.5 with a concentrated aqueous hydrochloric acid solution. Thereafter, 0.6 g of sodium acetate and 2.3 g of tetrabutylammonium bromide were added thereto and then 43.4 g of a toluene solution containing 34.9% of 3-[4-(1,1,2,2-tetrafluoroethoxy)-phenylthio]propanal were added thereto. The mixture was stirred at 45°–50° C. for 6 hours and then at room temperature for 12 hours. After the mixture had been neutralized with a concentrated aqueous hydrochloric acid solution, the organic layer was separated, washed with a saturated aqueous sodium chloride solution and then dried over anhydrous magnesium sulfate. Removing the solvent from the layer under reduced pressure gave 21.88 g of crude 4-hydroxy-6-[4-(1,1,2,2-tetrafluoroethoxy)phenylthio]-2-hexanone (purity: 70.9%, yield: 83.9%).

A purified product was obtained by recrystallization from a mixed solvent of diisopropyl ether and hexane. The purified product had a melting point of 55.0°-57 0° C.

PRODUCTION EXAMPLE 27

15.1 Grams of methyl acetoacetate were dissolved in 20 ml of water, and 19.4 g of a 28% aqueous sodium hydroxide solution were added thereto by drops while cooling the mixture to 35° C. or less. After having been stirred at 30°-35° C. for 3 hours, the mixture was adjusted to pH 7.5 with a concentrated aqueous hydrochloric acid solution. Thereafter, 1.64 g of sodium acetate and 6.44 g of tetrabutylammonium bromide were added thereto and then 60.3 g of a toluene solution containing 38.8% of 3-(4-trifluoromethylphenylthio)-butanal were added thereto. The mixture was stirred at 45°-50° C. for 10 hours and then at room temperature for 12 hours. After the mixture had been neutralized with a concentrated aqueous hydrochloric acid solution, the organic layer was separated, washed with a saturated aqueous sodium chloride solution and then dried over anhydrous magnesium sulfate. Removing the solvent from the layer under reduced pressure gave 34.24 g of crude 4-hydroxy-6-(4-trifluoromethylphenyl-thio)-2-heptanone (purity: 82.7%, yield: 99.0%).

A purified product was obtained by column chromatography. The purified product had an $n_D^{22}$ of 1.5042.

PRODUCTION EXAMPLE 28

The same procedure as in Production example 27 was repeated except that 59.6 g of a toluene solution containing 41.6% of 2-methyl-3-(4-trifluoromethylphenyl-thio)propanal was used in place of the toluene solution containing 3-(4-trifluoromethylphenylthio)butanal. Thus, 36.67 g of crude 4-hydroxy-5-methyl-6-(4-trifluromethylphenylthio)-2-hexanone were obtained (purity: 59.3%, yield: 71.1%).

A purified product was obtained by column chromatography. The purified product had an $n_D^{22}$ of 1.5058.

PRODUCTION EXAMPLE 29

3.77 Grams of methyl acetoacetate were dissolved in 5 ml of water, and 4.5 g of a 30% aqueous sodium hydroxide solution were added thereto by drops while cooling the mixture to 35° C. or less. After having been stirred at 30°-35° C. for 3 hours, the mixture was adjusted to pH 7.5 with a concentrated aqueous hydrochloric acid solution. Thereafter, 0.31 g of sodium acetate and 0.54 g of benzyltriethylammonium chloride were added thereto and then 14.7 g of a toluene solution containing 39.8% of 3-(4-trifluoromethylphenylthio)-propanal were added thereto. The mixture was stirred at 45°-50° C. for 6 hours and then at room temperature for 12 hours. After the mixture had been neutralized with a concentrated aqueous hydrochloric acid solution, the organic layer was separated, washed with a saturated aqueous sodium chloride solution and then dried over anhydrous magnesium sulfate. Removing the solvent from the layer under reduced pressure gave crude 4-hydroxy-6-(4-trifluoromethylphenylthio)-2-hexanone in a yield of 80.9%.

PRODUCTION EXAMPLE 30

9.86 Grams of methyl acetoacetate were dissolved in 15 ml of water, and 12.67 g of a 30% aqueous sodium hydroxide solution were added thereto by drops while cooling the mixture to 25° C. or less. After having been stirred at 30°-35° C. for 3 hours, the mixture was adjusted to pH 7.0 with a concentrated aqueous hydrochloric acid solution. Thereafter, 0.49 g of sodium acetate and 2.42 g of tetrabutylammonium bromide were added, and then an additional concentrated aqueous hydrochloric acid solution was added to the mixture so that the mixture was adjusted to pH 6.8. Further, 28.9 g of a toluene solution containing 40.5% of 3-(4-trifluoromethylphenylthio)propanal were added. The mixture was stirred at 45°-50° C. for 10 hours while maintaining the pH of the mixture at 7.2-7.3 with 2N hydrochloric acid. The organic layer was separated, washed with a 5% aqueous acetic solution and then with a saturated aqueous sodium chloride solution. Then the layer was dried over anhydrous magnesium sulfate. Removing the solvent from the layer under reduced pressure gave 16.1 g of crude 4-hydroxy-6-(4-trifluoromethylphenylthio)-2-hexanone (purity: 88.6%, yield: 97.8%).

COMPARATIVE EXAMPLE 1

1.51 Grams of methyl acetoacetate were dissolved in 2 ml of water, and 1.82 g of a 30% aqueous sodium hydroxide solution were added thereto by drops while cooling the mixture to 35° C. or less. After having been stirred at room temperature for 6 hours, the mixture was adjusted to pH 8 with concentrated aqueous hydrochloric acid solution. 0.20 Gram of 3-methylpiperidine was added thereto and then the mixture was adjusted to pH 6 with a concentrated aqueous hydrochloric acid solution. Thereafter, 4.5 g of a toluene solution containing 54.2% of 3-(4-trifluoromethylphenylthio)propanal were added thereto and the mixture was stirred at room temperature for 8 hours. After the mixture had been neutralized with a concentrated aqueous hydrochloric acid solution, the organic layer was separated, washed with a saturated aqueous sodium chloride solution and then dried over anhydrous magnesium sulfate. Removing the solvent from the layer under reduced pressure gave 2.90 g of a residue. Analyzing the residue by gas chromatography demonstrated that the yield of the desired product, 4-hydroxy-6-(4-trifluoromethylphenylthio)2-hexanone, was 10.6%; the dehydrated product thereof, 6-(4-trifluoromethylphenylthio)-3-hexen-2-one, 27.9%; the starting compound, 3-(4-trifluoromethylphenylthio)-propanal, 11.4%; and a by-product, 4,6-bis(4-trifluoromethylphenylthio)-2-hexanone, 27.0%.

COMPARATIVE EXAMPLE 2

1.51 Grams of methyl acetoacetate were dissolved in 2 ml of water, and 1.82 g of a 30% aqueous sodium hydroxide solution were added thereto by drops while cooling the mixture to 35° C. or less. After having been stirred at room temperature for 6 hours, the mixture was adjusted to pH 8 with a concentrated aqueous hydrochloric acid solution 0.20 Gram of triethylamine were added thereto and then the mixture was adjusted to pH 6 with a concentrated aqueous acid solution. Thereafter, 4.5 g of a toluene solution containing 54.2% of 3-(4-trifluoromethylphenylthio)propanal were added thereto and the mixture was stirred at room temperature for 8 hours. After the mixture had been neutralized with a concentrated aqueous hydrochloric acid solution, the organic layer was separated, washed with a saturated aqueous sodium chloride solution and then dried over anhydrous magnesium sulfate. Removing the solvent from the layer under reduced pressure gave 2.80 g of a residue. Analyzing the residue by gas chromatography demonstrated that the yield of the desired product, 4-hydroxy-6-(4-trifluoromethylphenylthio)-2-hexanone, was 30.6%; the dehydrated product thereof, 6-(4-trifluoromethylphenylthio)-3-hexen-2-one, 12.7%; the starting compound, 3-(4-trifluoromethylphenylthio)-propanal, 41.7%; and a by-product, 4,6-bis(4-trifluoromethylphenylthio)-2-hexanone, 0.7%.

COMPARATIVE EXAMPLE 3

1.51 Grams of methyl acetoacetate were dissolved in 2 ml of water, and 1.82 g of a 30% aqueous sodium hydroxide solution were added thereto by drops while cooling the mixture to 35° C. or less. After having been stirred at room temperature for 6 hours, the mixture was adjusted to pH 8 with a concentrated aqueous hydrochloric acid solution. 0.16 Gram of pyridine was added thereto and then the mixture was adjusted to pH 6 with a concentrated aqueous hydrochloric acid solution. Thereafter, 4.5 g of a toluene solution containing 54.2% of 3-(4-trifluoromethylphenylthio)propanal were added thereto and the mixture was stirred at room temperature for 8 hours. After the mixture had been neutralized with a concentrated aqueous hydrochloric acid solution, the organic layer was separated, washed with a saturated aqueous sodium chloride solution and then dried over anhydrous magnesium sulfate. Removing the solvent from the layer under reduced pressure gave 2.55 g of a residue. Analyzing the residue by gas chromatography demonstrated that the yield of the desired product, 4-hydroxy-6-(4-trifluoromethylphenylthio)-2-hexanone, was 8.1%; the dehydrated product thereof, 6-(4-trifluoromethylphenyl-thio)-3-hexen-2-one, 9.8%; the starting compound, 3-(4-trifluoromethylphenylthio)-propanal, 66.7%; and a by-product, 4,6-bis(4-trifluoromethylphenylthio)-2-hexanone, 1.1%.

Next, production of the $\alpha,\beta$-unsaturated ketone compounds (III) from the hydroxyketones (I) will be shown with reference to the following production examples.

PRODUCTION EXAMPLE 31

20.75 Grams of 4-hydroxy-6-44-trifluoromethylphenylthio)-2-hexanone were dissolved in 100 ml of toluene, and 1.00 g of oxalic acid was added thereto. The resulting mixture was refluxed for 1.25 hours with stirring. After having been cooled, the mixture was washed with a saturated aqueous sodium hydrogencarbonate solution and then with a saturated aqueous sodium chloride solution. Then the mixture was dried over anhydrous magnesium sulfate. Removing the solvent from the mixture under reduced pressure gave 17.13 g of 6-(4-trifluoromethylphenylthio)-3-hexen-2-one (trans : cis =3.7 : 1) (purity: 97.8%). The product was further column chromatographed to obtain a purified product having a refractive index ($n_D{}^{20}$) of 1.5274. The yield was 86.0%.

PRODUCTION EXAMPLE 32

1.46 Grams of 4-hydroxy-6-(4-trifluoromethylphenylthio)-2-hexanone were dissolved in 12 ml of an aqueous solution of acetic acid and the mixture was refluxed for 1 hour with stirring. After having been cooled, the mixture was washed with a saturated aqueous sodium hydrogencarbonate solution and then with a saturated aqueous sodium chloride solution. Then the mixture was dried over anhydrous magnesium sulfate. Removing the solvent from the mixture under reduced pressure gave 1.27 g of 6-(4-trifluoromethylphenylthio)-3-hexen-2-one (trans : cis =6.5 : 1) (purity: 74.7%). The yield was 69.3%. Percent recovery of the starting material was 11.4%.

PRODUCTION EXAMPLE 33

13.53 Grams of 4-hydroxy-6-(2-trifluoromethylphenylthio)-2-hexanone were dissolved in 150 ml of toluene, and 0.71 g of oxalic acid was added thereto. The resulting mixture was refluxed for 3.5 hours with stirring. After having been cooled, the mixture was washed with a saturated aqueous sodium hydrogencarbonate solution and then with a saturated aqueous sodium chloride solution. Then the mixture was dried over anhydrous magnesium sulfate. Removing the solvent from the mixture under reduced pressure gave 12.93 g of 6-(2-trifluoromethylphenylthio)-3-hexen-2-one (trans : cis =4.4 : 1) (purity: 97.6%). The product was further column chromatographed to obtain a purified product having a refractive index ($n_D{}^{19}$) of 1.5263. The yield was 99.4%.

PRODUCTION EXAMPLE 34

5.00 Grams of 4-hydroxy-6-(4-trifluoromethylphenylthio)-2-hexanone were dissolved in 50 ml of toluene, and 1.00 g of trichloroacetic acid was added thereto. The resulting mixture was refluxed for 2 hours with stirring. After having been cooled, the mixture was washed with a saturated aqueous sodium hydrogencarbonate solution and then with a saturated aqueous sodium chloride solution. Then the mixture was dried over anhydrous magnesium sulfate. Removing the solvent from the layer under reduced pressure gave 6-(4-trifluoromethylphenylthio)-3-hexen-2-one (trans : cis =8.1 : 1) having a purity of 72.4%. Percent recovery of the starting material was 4.3%.

PRODUCTION EXAMPLE 35

12.48 Grams of 4-hydroxy-6-[4-(1,1,2,2-tetrafluoroethoxy)phenylthio]-2-hexanone were dissolved in 150 ml of toluene, and 1.50 g of oxalic acid were added thereto. The resulting mixture was refluxed for 2 hours with stirring, allowed to cool and then treated in the same manner as in Production example 34. Thus, 11.76 g of 6-[4-(1,1,2,2-tetrafluoroethoxy)phenylthio]-3-hexen-2-one (trans : cis =4.6 : 1) were obtained (purity: 98.0%). Further, the product was column chromatographed to obtain a purified product having a refractive index ($n_D{}^{23}$) of 1.5202. The yield was 96.8%.

PRODUCTION EXAMPLE 36

5.84 Grams of 4-hydroxy-6-(3-trifluoromethylphenylthio)-2-hexanone were dissolved in 58 ml of toluene, and 0.62 g of oxalic acid was added thereto. The resulting mixture was refluxed for 4 hours with stirring, allowed to cool and then treated in the same manner as in Production example 34. Thus, 5.26 g of 6-(3-trifluoromethylphenylthio)-3-hexen-2-one (trans : cis =2.9 : 1) were obtained (purity: 98.5%). Further, the product was column chromatographed to obtain a purified product having a refractive index (n25.5) of 1.5222. The yield was 94.5%.

PRODUCTION EXAMPLE 37

0.5 Gram of 4-hydroxy-6-(4-trifluoromethylphenylthio)-2-hexanone was dissolved in 10 ml of toluene, and 0.38 g of silica gel was added thereto. The resulting mixture was refluxed for 8 hours with stirring, allowed to cool and then treated in the same manner as in Production example 34. Thus, 6-(4-trifluoromethylphenylthio)-3-hexen-2-one was obtained (purity: 77.0%).

PRODUCTION EXAMPLE 38

0.5 Gram of 4-hydroxy-6-(4-trifluoromethylphenylthio)-2-hexanone was dissolved in 30 ml of toluene, and 0.5 g of metaboric acid was added thereto. The resulting mixture was refluxed for 7 hours with stirring, allowed to cool and then treated in the same manner as in Production example 34. Thus, 6-(4-trifluoromethylphenylthio)-3-hexen-2-one (almost all of it were trans isomers) was obtained (purity: 93.1%).

PRODUCTION EXAMPLE 39

0.5 Gram of 4-hydroxy-6-(4-trifluoromethylphenylthio)-2-hexanone was dissolved in 30 ml of chlorobenzene, and 0.5 g of oxalic acid was added thereto. The resulting mixture was refluxed for 5 hours with stirring. Analyzing the refluxed mixture by gas chromatography demonstrated that 6-(4-trifluoromethylphenylthio)-3-hexen-2-one was quantitatively obtained.

PRODUCTION EXAMPLE 40

1.46 Grams of 4-hydroxy-6-(4-trifluoromethylphenylthio)-2-hexanone were dissolved in 15 ml of toluene, and 0.35 g of concentrated aqueous sulfuric acid solution was added thereto. The resulting mixture was refluxed for 15 minutes with stirring, allowed to cool and then treated in the same manner as in Production example 34. Thus, 1.15 g of 6-(4-trifluoromethylphenylthio)-3-hexen-2-one (trans cis =4.2 : 1) were obtained (purity: 68.0%). The yield was 57.1%. Percent recovery of the starting material was 32.0%.

PRODUCTION EXAMPLE 41

0.3 Gram of 4-hydroxy-6-(4-trifluoromethylphenylthio)-2-hexanone was dissolved in 30 ml of toluene, and 0.004 g of p-toluenesulfonic acid was added thereto. The resulting mixture was refluxed for 30 minutes with stirring, allowed to cool and then treated in the same manner as in Production example 34. Thus, 6-(4-trifluoromethylphenylthio)-3-hexen-2-one was obtained (purity: 98.5%).

PRODUCTION EXAMPLE 42

1.96 Grams of 4-hydroxy-6-(4-trifluoromethylphenylthio)-2-hexanone were dissolved in 30 ml of toluene, and 0.04 g of p-toluenesulfonic acid was added thereto. The resulting mixture was refluxed for 2.5 hours with stirring, allowed to cool and then treated in the same manner as in Production example 34. Thus, 6-(4-trifluoromethylphenylthio)-3-hexen-2-one was obtained (purity: 95.1%).

PRODUCTION EXAMPLE 43

0.5 Gram of 4-hydroxy-6-(4-trifluoromethylphenylthio)-2-hexanone was dissolved in 10 ml of toluene, and 0.26 g of Nafion ® was added thereto. The resulting mixture was refluxed for 6 hours with stirring, allowed to cool and then treated in the same manner as in Production example 34. Thus, 6-(4-trifluoromethylphenylthio)-3-hexen-2-one was obtained (purity: 78.0%).

PRODUCTION EXAMPLE 44

13.58 Grams of 4-hydroxy-6-(4-trifluoromethylphenylthio)-2-heptanone were dissolved in 150 ml of toluene, and 1.0 g of oxalic acid was added thereto. The resulting mixture was refluxed for 2.5 hours with stirring, allowed to cool and then treated in the same manner as in Production example 34. Thus, 12.65 g of 6-(4-trifluoromethylphenylthio)-3-hepten-2-one (trans : cis =6.7 : 1) was obtained (purity: 95.4%) having an $n_D^{21}$ of 1 5101. The yield was 94.7%.

PRODUCTION EXAMPLE 45

15.21 Grams of 4-hydroxy-5-methyl-6-(4-trifluoromethylphenylthio)-2-hexanone were dissolved in 150 ml of toluene, and 2.0 g of oxalic acid were added thereto. The resulting mixture was refluxed for 3 hours with stirring, allowed to cool and then treated in the same manner as in Production example 34. Thus, 12.67 g of 5-methyl-6-(4-trifluoromethylphenylthio)-3-hexen-2-one (almost all of it were trans isomers) was obtained (purity: 94.8%) having an $n_D^{23}$ of 1.5077. The yield was 84.2%.

PRODUCTION EXAMPLE 46

3.00 Grams of 4-hydroxy-6-(4-trifluoromethylphenylthio)-2-hexanone were dissolved in 50 ml of toluene, and 0.30 g of boric acid was added thereto. The resulting mixture was refluxed for 8 hours with stirring. The refluxed mixture, after allowed to cool, was washed with a saturated aqueous sodium hydrogen-carbonate solution and then with a saturated aqueous sodium chloride solution. Then the mixture was dried over anhydrous magnesium sulfate. Removing the solvent from the mixture under reduced pressure gave 2.85 g of 6-(4-trifluoromethylphenylthio)-3-hexen-2-one (trans : cis =28.6 : 1)(purity: 97.7%). The yield was 98.7%.

PRODUCTION EXAMPLE 47

0.85 Gram of boric acid was added to 80 ml of toluene, and the resulting mixture was refluxed for 3 hours with stirring and then cooled to 30° C. A solution of 6.00 g of 4-hydroxy-6-(4-trifluoromethylphenylthio)-2-hexanone in 20 ml of toluene was added thereto, and the resulting mixture was further refluxed for 8 hours with stirring. The refluxed mixture was washed three times with hot water and then dried over anhydrous magnesium sulfate. Removing the solvent from the mixture under reduced pressure gave 5.58 g of 6-(4-trifluoromethylphenylthio)-3-hexen-2-one (trans : cis =38.7 : 1) (purity: 99.3%). The yield was 98.4%.

PRODUCTION EXAMPLE 48

0.85 Gram of boric acid was added to 80 ml of toluene, and the resulting mixture was refluxed for 3 hours with stirring. Thereafter, a solution of 6.00 g of 4-hydroxy-6-(4-trifluoromethylphenylthio)-2-hexanone in 20 ml of toluene was added dropwise thereto at the same refluxing temperature as the toluene solution of boric acid had been refluxed. And the mixture was further refluxed for 8 hours with stirring. The reaction mixture was washed three times with hot water and dried over anhydrous magnesium sulfate. Removing the solvent from the mixture under reduced pressure gave 5.40 g of 6-(4-trifluoromethylphenylthio)-3-hexen-2-one (trans : cis =38.8 : 1) (purity: 99.4). The yield was 95.4%.

PRODUCTION EXAMPLE 49

3.00 Grams of 4-hydroxy-6-(4-trifluoromethylphenylthio)-2-hexanone were dissolved in 50 ml to toluene, and 0.50 g of 85% phosphoric acid, was added thereto. The resulting mixture was refluxed for 1 hour with stirring. After having been cooled, the mixture was washed with a saturated aqueous sodium hydrogencarbonate solution and then with a saturated aqueous sodium chloride solution. Then the mixture was dried over anhydrous magnesium sulfate. Removing the solvent from the mixture under reduced pressure gave 2.83 g of 6-(4-trilfuoromethylphenylthio)-3-hexen-2-one (trans cis =2.8 : 1) (purity: 84.2%). The yield was 84.7%.

PRODUCTION EXAMPLE 50

3.00 Grams of 4-hydroxy-6-(4-trifluoromethylphenylthio)-2-hexanone were dissolved in 50 ml of toluene, and 0.15 g of polyphosphoric acid was added thereto. The resulting mixture was refluxed for 30 minutes with stirring. Removing the solvent from the mixture was washed with a saturated aqueous sodium hydrogencarbonate solution and then with a saturated aqueous sodium chloride solution. Then the mixture was dried over anhydrous magnesium sulfate. Removing the solvent from the mixture under reduced pressure gave 2.69 g of 6-(4-trifluoromethylphenylthio)-3-hexen-2-one (trans : cis =14.6 : 1) (purity: 76.5%). The yield was 73.3%.

PRODUCTION EXAMPLE 51

1.50 Grams of 6-(4-bromophenylthio)-4-hydroxy-2-hexanone were dissolved in 100 ml of toluene, and 0.07 g of p-toluene sulfonic acid was added thereto. The resulting mixture was refluxed for 2.5 hours with stirring. After having been cooled, the mixture was washed with a saturated aqueous sodium hydrogencarbonate solution and then saturated aqueous sodium chloride solution. Then the mixture was dried over anhydrous magnesium sulfate. Removing the solvent from the mixture under reduced pressure gave 1.41 g of 6-(4-bromophenylthio)-3-hexen-2-one. (trans : cis =2.8 : 1) (purity: 95.1%). The yield was 95.1%.

PRODUCTION EXAMPLE 52

1.00 Gram of 6-(2-fluorophenylthio)-4-hydroxy-2-heptanone was dissolved in 100 ml of toluene, and 0.02 g of p-toluene sulfonic acid was added thereto. The resulting mixture was refluxed for 2 hours with stirring. After having been cooled, the mixture was washed with a saturated aqueous sodium hydrogencarbonate solution and then saturated aqueous sodium chloride solution. Then the mixture was dried over anhydrous magnesium sulfate. Removing the solvent from the mixture under reduced pressure gave 0.84 g of 6-(2-fluorophenylthio)-3-hepten-2-one. (trans : cis =5.1 : 1) (purity: 80.6%). The yield was 73.1%.

PRODUCTION EXAMPLE 53

1.00 Gram of 6-(3-fluorophenylthio)-4-hydroxy-2-heptanone was dissolved in 100 ml of toluene, and 0.02 g of p-toluene sulfonic acid was added thereto. The resulting mixture was refluxed for 2.5 hours with stirring. After having been cooled, the mixture was washed with a saturated aqueous sodium hydrogencarbonate solution and then saturated aqueous sodium chloride solution. Then the mixture was dried over anhydrous magnesium sulfate. Removing the solvent from the mixture under reduced pressure gave 0.96 g of 6-(3-fluorophenylthio)-3-hepten-2-one. (trans : cis =5.6 : 1) (purity: 89.3%). The yield was 92.5%.

PRODUCTION EXAMPLE 54

1.00 Gram of 6-(3-chlorophenylthio)-4-hydroxy-5-methyl-2-hexanone was dissolved in 100 ml of toluene, and 0.02 g of p-toluene sulfonic acid was added thereto. The resulting mixture was refluxed for 1.5 hours with stirring. After having been cooled, the mixture was washed with a saturated aqueous sodium hydrogencarbonate solution and then saturated aqueous sodium chloride solution. Then the mixture was dried over anhydrous magnesium sulfate. Removing the solvent from the mixture under reduced pressure gave 1.05 g of 6-(3-chlorophenylthio)-5-methyl-3-hexen-2-one. (trans : cis =5.7 : 1) (purity: 88.6%). The yield was 98.9%.

PRODUCTION EXAMPLE 55

1.00 Gram of 4-hydroxy-6-(2-methylphenylthio)-2-hexanone was dissolved in 100 ml of toluene, and 0.02 g of p-toluene sulfonic acid was added thereto. The resulting mixture was refluxed for 2.5 hours with stirring. After having been cooled, the mixture was washed with a saturated aqueous sodium hydrogencarbonate solution and then saturated aqueous sodium chloride solution. Then the mixture was dried over anhydrous magnesium sulfate. Removing the solvent from the mixture under reduced pressure gave 0.97 g of 6-(2-methylphenylthio)-3-hexen-2-one. (trans : cis =3.8 : 1) (purity: 94.7%). The yield was 99.8%.

PRODUCTION EXAMPLE 56

1.00 Gram of 4-hydroxy-6-(4-methylphenylthio)-2-heptanone was dissolved in 100 ml of toluene, and 0.02 g of p-toluene sulfonic acid was added thereto. The resulting mixture was refluxed for 2.5 hours with stirring. After having been cooled, the mixture was washed with a saturated aqueous sodium hydrogencarbonate solution and then saturated aqueous sodium chloride solution. Then the mixture was dried over anhydrous magnesium sulfate. Removing the solvent from the mixture under reduced pressure gave 0.74 g of 6-(4-methylphenylthio)-3-hexen-2-one. (trans : cis =5.5 : 1) (purity: 83.5%). The yield was 66.7%.

PRODUCTION EXAMPLE 57

1.00 Gram of 4-hydroxy-6-(2-methoxyphenylthio)-2-hexanone was dissolved in 100 ml of toluene, and 0.02 g of p-toluene sulfonic acid was added thereto. The resulting mixture was refluxed for 1 hour with stirring. After having been cooled, the mixture was washed with a saturated aqueous sodium hydrogencarbonate solution and then saturated aqueous sodium chloride solution. Then the mixture was dried over anhydrous magnesium sulfate. Removing the solvent from the mixture under reduced pressure gave 0.96 g of 6-(2-methoxyphenylthio)-3-hexen-2-one. (trans : cis =6.6 : 1) (purity: 91.9%). The yield was 94.6%.

PRODUCTION EXAMPLE 58

1.00 Gram of 4-hydroxy-6-(3-methoxyphenylthio)-2-hexanone was dissolved in 100 ml of toluene, and 0.02 g of p-toluene sulfonic acid was added thereto. The resulting mixture was refluxed for 2.5 hours with stirring.

After having been cooled, the mixture was washed with a saturated aqueous sodium hydrogencarbonate solution and then saturated aqueous sodium chloride solution. Then the mixture was dried over anhydrous magnesium sulfate. Removing the solvent from the mixture under reduced pressure gave 0.96 g of 6-(3-methoxyphenylthio)-3-hexen-2-one. (trans : cis =4.2 : 1) (purity: The yield was 90.3%.

PRODUCTION EXAMPLE 59

1.00 Gram of 4-hydroxy-6-(3-methoxyphenylthio)-2-heptanone was dissolved in 100 ml of toluene, and 0.02 g of p-toluene sulfonic acid was added thereto. The resulting mixture was refluxed for 1 hour with stirring. After having been cooled, the mixture was washed with a saturated aqueous sodium hydrogencarbonate solution and then saturated aqueous sodium chloride solution. Then the mixture was dried over anhydrous magnesium sulfate. Removing the solvent from the mixture under reduced pressure gave 1.05 g of 6-(3-methoxyphenylthio)-3-hepten-2-one. (trans : cis =4.8 : 1) (purity: 82.7%). The yield was 93.5%.

PRODUCTION EXAMPLE 60

1.00 Gram of 6-(4-fluorophenylthio)-4-hydroxy-5-methyl-2-hexanone was dissolved in 100 ml of toluene, and 0.02 g of p-toluene sulfonic acid was added thereto. The resulting mixture was refluxed for 1.5 hours with stirring. After having been cooled, the mixture was washed with a saturated aqueous sodium hydrogencarbonate solution and then saturated aqueous sodium chloride solution. Then the mixture was dried over anhydrous magnesium sulfate. Removing the solvent from the mixture under reduced pressure gave 1.08 g of 6-(4-fluorophenylthio)-5-methyl-3-hexen-2-one. (trans : cis =3.7 : 1) (purity: 83.5%). The yield was 96.8%.

PRODUCTION EXAMPLE 61

1.00 Gram of 4-hydroxy-6-(2-methylphenylthio)-2-heptanone was dissolved in 100 ml of toluene, and 0.02 g of p-toluene sulfonic acid was added thereto. The resulting mixture was refluxed for 1.5 hours with stirring. After having been cooled, the mixture was washed with a saturated aqueous sodium hydrogencarbonate solution and then saturated aqueous sodium chloride solution. Then the mixture was dried over anhydrous magnesium sulfate. Removing the solvent from the mixture under reduced pressure gave 0.98 g of 6-(2-methylphenylthio)-3-hepten-2-one. (trans : cis =7.0 : 1) (purity: 81.5%). The yield was 86.0%.

PRODUCTION EXAMPLE 62

15.51 Grams of 6-(4-chlorophenylthio)-4-hydroxy-2-hexanone was dissolved in 100 ml of toluene, and 0.92 g of oxalic acid was added thereto. The resulting mixture was refluxed for 4 hours with stirring. After having been cooled, the mixture was washed with a saturated aqueous sodium hydrogencarbonate solution and then saturated aqueous sodium chloride solution. Then the mixture was dried over anhydrous magnesium sulfate. Removing the solvent from the mixture under reduced pressure gave 14.22 g of 6-(4-chlorophenyl-thio)-3-hexen-2-one. (trans : cis =3.1 : 1) (purity: 98.0%). The yield was 96.6%. A purified product was obtained by column chromatography. The purified product had an $n_D^{24}$ of 1.5953.

COMPARATIVE EXAMPLE 4

10.0 Grams of 4-hydroxy-6-(4-trifluoromethylphenylthio)-2-hexanone were dissolved in 100 ml of toluene, and 1.50 g of phthalic acid were added thereto. The resulting mixture was refluxed for 1.5 hours with stirring, allowed to cool and then treated in the same manner as in Production example 34. However, the starting material was remained unreacted and was quantitatively recovered.

COMPARATIVE EXAMPLE 5

5.84 Grams of 4-hydroxy-6-(4-trifluoromethylphenylthio)-2-hexanone were dissolved in 50 ml of toluene, and 0.33 g of 4-nitrobenzoic acid was added thereto. The resulting mixture was refluxed for 1 hour with stirring, allowed to cool and then treated in the same manner as in Production example 34. However, the starting material was remained unreacted and was quantitatively recovered.

COMPARATIVE EXAMPLE 6

5.0 Grams of 4-hydroxy-6-(4-trifluoromethylphenylthio)-2-hexanone were dissolved in 50 ml of toluene, and 0.42 g of 3,5-dinitrobeznoic acid was added thereto. The resulting mixture was refluxed for 1 hour with stirring, allowed to cool and then treated in the same manner as in Production example 34. However, the starting material was remained unreacted and was quantitatively recovered.

COMPARATIVE EXAMPLE 7

10.00 Grams of 4-hydroxy-6-(4-trifluoromethylphenylthio)-2-hexanone were dissolved in 100 ml of toluene, and 1.5 g of succinic acid were added thereto. The resulting mixture was refluxed for 1.5 hours with stirring, allowed to cool and then treated in the same manner as in Production example 34. However, the starting material was remained unreacted and was quantitatively recovered.

COMPARATIVE EXAMPLE 8

5 84 Grams of 4-hydroxy-6-(4-trifluoromethylphenylthio)-2-hexanone were dissolved in 50 ml of toluene, and 0.19 g of phenol was added thereto. The resulting mixture was refluxed for 1 hour with stirring, allowed to cool and then treated in the same manner as in Production example 34. However, the starting material was remained unreacted and was quantitatively recovered.

COMPARATIVE EXAMPLE 9

21.4 Grams of 4-hydroxy-6-(4-trifluoromethylphenylthio)-2-hexanone were dissolved in 200 ml of toluene, and 1.5 g of malonic acid were added thereto. The resulting mixture was refluxed for 1.5 hours with stirring, allowed to cool and then treated in the same manner as in Production example 34. Analyzing the resulting product by gas chromatography, demonstrated that the product contained only 19.5% of 6-(4-trifluoromethylphenylthio)-3-hexen-2-one (trans : cis =4.4 : 1), which is a desired product, and that 42.8% of the starting material were remained unreacted.

What is claimed is:

1. A compound represented by the formula,

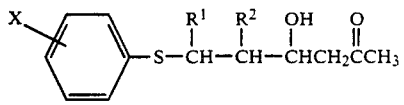
wherein X represents a lower alkyl, lower alkoxy, lower haloalkyl or lower haloalkoxy group or a halogen atom, and $R^1$ and $R^2$, which may be the same or different, represent a hydrogen atom or a methyl group.
2. A compound according to claim 1, wherein X is a trifluoromethyl group.
* * * * *